United States Patent [19]

Tomimasu et al.

[11] Patent Number: 4,975,578

[45] Date of Patent: Dec. 4, 1990

[54] METHOD AND APPARATUS FOR DETERMINING DISTRIBUTION OF MASS DENSITY

[75] Inventors: Hiroshi Tomimasu; Philip Luner, both of Syracuse, N.Y.

[73] Assignee: The Research Foundation of State University of NY, Albany, N.Y.

[21] Appl. No.: 339,211

[22] Filed: Apr. 17, 1989

[51] Int. Cl.$^5$ .............................................. G01N 9/00
[52] U.S. Cl. .................................. 250/306; 250/307; 250/311; 250/397
[58] Field of Search ............... 250/306, 307, 308, 311, 250/392

[56] References Cited

U.S. PATENT DOCUMENTS

| | | | |
|---|---|---|---|
| 1,991,599 | 2/1935 | Davis et al. | 356/426 |
| 3,413,192 | 11/1968 | Beecher | 162/259 |
| 3,489,901 | 1/1970 | Brown | 250/308 |
| 3,833,811 | 9/1974 | Koike et al. | 250/306 |
| 4,038,543 | 7/1977 | Krisch et al. | 250/307 |
| 4,189,641 | 2/1980 | Katagiri et al. | 250/306 |
| 4,376,891 | 3/1983 | Rauscher et al. | 250/307 |
| 4,382,182 | 5/1983 | Matsuzaka et al. | 250/307 |
| 4,634,868 | 1/1987 | Delacy | 250/306 |
| 4,644,174 | 2/1987 | Oullette et al. | 250/559 |
| 4,707,223 | 11/1987 | Sabater et al. | 162/262 |
| 4,831,255 | 5/1989 | Krivanek | 250/306 |

OTHER PUBLICATIONS

Twing-Albert test method, Tappi method UM432.
Burkhard et al., "A Formation Tester which Graphically Records Paper Structure", Pulp and Paper Magazine of Canada, vol. 61, p. T319, Jun. 1960.
Herdman and Corte, "Comments of the Distribution of Mass Density of Paper", Journal of Pulp and Paper Science, vol. 81, p. T261, Oct. 1980.
Balodis, Appita, vol. 18, p. 184, May 1965.
Attwood and Parker, "Basis Weight Variations over Small areas of Paper", Paper Technology, vol. 3, p. 435, May 1962.
Marton and Schiff, "Determination of Object Thickness in Electron Microscopy", Journal of Applied Physics, vol. 12, p. 759, Oct. 1941.
Zeitler and Bahr, "A Photometric Procedure for Weight Determination of Sub-Microscopic Particles Quantitative Electron Microscopy", Journal of Applied Physics, vol. 33, p. 847, Mar. 1962.
Gatan product literature Model 673–Wide Angle TV for TEM.
Gatan product literature Model 622–Fiber Optically Coupled TV System for TEM.

*Primary Examiner*—Jack I. Berman
*Assistant Examiner*—Kiet T. Nguyen
*Attorney, Agent, or Firm*—Heslin & Rothenberg

[57] ABSTRACT

Distribution of mass density of paper or other materials is determined by irradiating a sample with a burst of electron beams from an electron gun. The intensity levels of electron beams emerging from said sample are detected by an areal detector located immediately behind the sample. These intensity levels are processed to derive distribution of mass density information for the sample. The electron beam detector may be a photographic film or a realtime electron beam detector assembly coupled to computer controlled digital data processing and displaying equipment.

23 Claims, 5 Drawing Sheets fig. 1a fig. 1b fig. 2a fig. 2b fig. 3 fig. 6 fig. 4a fig. 4b fig. 5

METHOD AND APPARATUS FOR DETERMINING DISTRIBUTION OF MASS DENSITY

BACKGROUND OF THE INVENTION

This invention relates generally to the field of nondestructive testing, and more particularly to a method and apparatus for measuring the distribution of mass density of materials, especially paper and paper board, using electron beams.

Paper is made of a great number of fibers and the uniformity of the fiber distribution is a very important factor which determines the paper's properties such as strength, smoothness, and printability. The uniformity of the fiber distribution is determined while the fiber suspension is delivered to the drainage section of the paper machine or in the drainage section itself. The uniformity of the fiber distribution is called "formation" and is usually evaluated by its "look-through" appearance when held up to the light. A variety of terms such as "flocced", "cloudy", "uneven", "uniform", etc. are used to describe formation Since formation is usually evaluated by visual perception, the evaluation is not absolute or objective. Many attempts have been made to measure the uniformity of fiber distribution objectively. An early scanning device based on the transmission of light through a rotating disc of paper can be found in U.S. Pat. No. 1,991,599 of Davis et al. Many variations of this original design have been proposed. Among the most important ones are the Thwing-Albert test method and the Quebec North Shore Mead (QNSM) tester. In the mill, on-line formation meters based on light transmission such as described in U.S. Pat. No. 4,644,174 of Ouellette et al. and U.S. Pat. No. 4,707,223 of Sabater et al. are being used to assess formation in the paper.

However, light transmission in paper is affected by many factors such as the degree of bonding, pressing and the presence of scattering fillers. Other methods for assessing mass variations rather than opacity variations should therefore be used to determine the fiber distribution within the sheet. Herdman and Corte in volume 81 of the *Pulp and Paper Canada*, P.T261, October, 1980, introduced the distribution of mass density approach. In their work, beta-radiation was used in place of visible light. Since beta-rays are attenuated and absorbed in matter, their absorption is related to the amount of mass being traversed. The density of mass distribution is therefore a true basis weight representation.

In laboratories, the distribution of mass density of paper may be obtained by measuring the attenuation of beta-particles directly as a strip of paper is scanned as presented by Balodis (Appita, Vol. 18, page 184, May, 1965). This is a slow and tedious operation, especially if the source is weak and/or very small areas need to be scanned. A much quicker way is to obtain a beta-radiograph of paper as presented by Attwood and Parker ("Basis Weight Variations Over Small Areas of Paper", Paper Technology, Vol. 3, P. 435, May, 1962). This is done by sandwiching a paper sample between a radioactive plastic $^{14}C$ source and a photographic film. On developing the film with a suitable calibration, the distribution of mass density can be calculated from optical density measurements. This method may take 4 to 24 hours and the distribution of mass density of thick paper samples ($>150$ g/m$^2$) cannot be determined by this method.

In the mill, beta-gages described as in U.S. Pat. No. 3,413,192 of Beecher and U.K. Pat. No. 1,271,438 are being used for measuring the distribution of mass density in paper. This system usually measures larger areas as large as 25 cm$^2$ and gives the average and the variation of the basis weight, the unit of which is g/m$^2$, but does not give the variation in smaller areas of the sample. Since these techniques use open beta-radiation sources, it can be dangerous for the operators to expose themselves to the radiation. Therefore, another method to measure the distribution of mass density, which is rapid, safe, accurate, applicable to a wide range of basis weight and yet capable of detecting small scale variations, would be a significal advantage in both industrial and laboratory settings.

In the field of electron microscopy, a technique to measure the thickness or the density of a very thin sample by Transmission Electron Microscopy was developed by Marton and Schiff ("Determination of Object Thickness in Electron Microscopy", Journal of Applied Physics, Vol. 12, P. 759, October, 1941). This technique has been used to determine the thickness and the density of biological samples and synthetic lattices placed in a conventional sample chamber at the focal plane of a transmission electron microscope, with a magnified image of the sample being analyzed. However, according to Zeitler and Bahr, ("A Photometric Procedure for Weight Determination of Submicroscopic Particles Quantitative Electron Microscopy", Journal of Applied Physics, Vol. 33, P. 847, March, 1962), this technique has a limitation in sample thickness. Only a sample which is less than 0.4 microns in thickness can be measured by this method. Paper samples are far thicker than this and cannot be measured by this method.

SUMMARY OF THE INVENTION

In accordance with the principles of the present invention, distribution of mass density in a sample of paper or other organic material, or in inorganic materials such as ceramics, glasses, and metal foils, is rapidly, accurately and safely obtained by measuring the attenuation of electron beams traversing the sample. The sample is exposed to a burst of electron beams, preferable in the range of 50 keV to 200 keV, generated by an electron gun and the attenuation of the electron beams by the sample is recorded by an areal detector located immediately behind the sample. In the presently preferred embodiment, this process is accomplished in a vacuum environment. The attenuated intensity of the electron beams detected by the detector is then converted into mass density information through an appropriate calibration process.

The invention can be implemented using a photographic media as the electron beam detector. The media is developed in known fashion and the optical densities of the developed film, which correspond to the attenuated intensity levels of the electron beams, can be digitized for further processing. Alternatively, a real time detector assembly coupled to a computer controlled digital data processing and areal information displaying subsystem can be employed. The sample can be exposed to a uniform intensity distribution of electron beams, or the burst of electron beams may include beams of different energy levels. In another aspect of the invention, a calibration wedge containing sites of known different basis weight having a similar mass absorption coefficient to that of the sample, is simultaneously exposed to the electron beams with the sample, to provide reference levels for basis weight calibration of the sample. The invention also contemplates the possibility of using a high intensity electron gun in air, as an alternative to creating a vacuum environment along the pathway of the electron beams.

The method of the present invention is applicable to samples which are more than 1 cm×1 cm in size and more than 1 μm in thickness, which are impossible to analyze by the existing electron microscopy techniques. The required measuring time is reduced to about 1 second or less to obtain the image of the attenuation of electron beams over the whole area of the sample, which is 1,000 to 10,000 times faster than the common beta-radiograph technique. The new method provides finer information on the structure of paper, better image contrast and less health hazard than other methods. It is also applicable to a wider range of basis weight and readily lends itself to real-time data processing and the possibility of on-line measurement. Another advantage is the provision of accurate, objective measurements at relatively low cost.

BRIEF DESCRIPTION OF THE DRAWINGS

These and other objects, features and advantages of the present invention will be more fully understood from the following detailed description when read in conjunction with the accompanying drawings, in which.

DETAILED DESCRIPTION

The present invention is directed generally to a method for determining distribution of mass density of a sample, which includes the steps of: irradiating a test area of a sample with a burst of electron beams from an electron gun; detecting intensity levels of electron beams emerging from the test area with a detector located immediately behind the test area; and processing the intensity levels to provide distribution of mass density information for the test area of the sample. Several embodiments of apparatus for advantageously implementing this method will now be described. Although presented primarily in terms of determining formation of paper, this technique may be applied to other materials, especially of organic origin. The inventors have so imaged mylar, kevlar, foams, and graphite. Imaging of these materials can be used as a means of inspection and identifying defects.

Figure 1A:
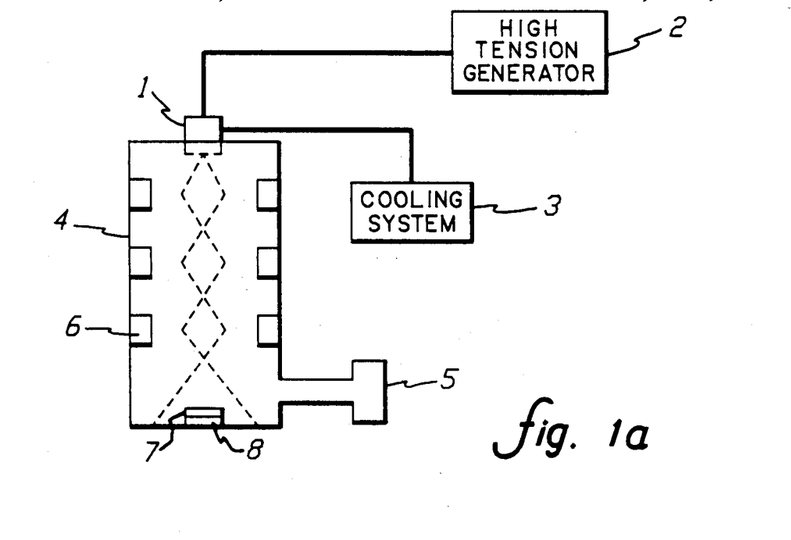
FIG. 1a is a schematic illustration of a system using a photographic film as an electron beam detector to measure the distribution of mass density of paper samples by electron beams, in accordance with the principles of the present invention.

FIG. 1a shows schematically a system to measure the distribution of mass density of paper samples by electron beams, which uses a photographic film as an electron beam detector. In this embodiment, a sample 7 is placed on a photographic film 8 in a vacuum chamber 4 which is evacuated by a vacuum pump system 5. Substantially mono-energetic electron beams are generated by the electron gun 1 which is supplied with high voltage by a high tension generator 2 and with cooling water or oil by a cooling system 3. A burst of electron beams generated by the electron gun travel in the vacuum chamber and can be focused by an optional electromagnetic lens system 6, as shown, to provide a uniform intensity distribution of electron beams over either the whole sample or a designated test area of the sample. While traversing the sample, the electron beams are attenuated by scattering and absorption. The attenuated intensity levels of the electron beams emerging from different points of the test area of the sample are recorded on the photographic film and the film is processed, i.e. developed, in a standard fashion. Preferably, a standard calibration wedge which has several reference sites of plastic films such a mylar, cellulose acetate, cellophane or thin metal foils such as aluminum having different known basis weight and similar mass absorption coefficient to that of paper is exposed to the electron beams with the sample, as a reference for the basis weight calibration.

Figure 5:
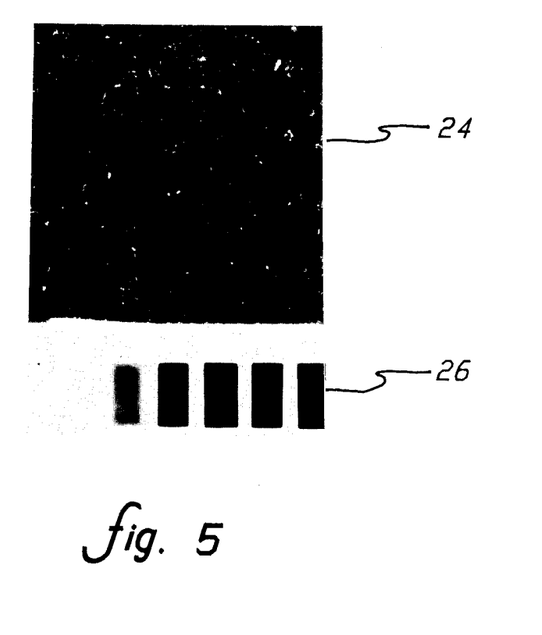
FIG. 5 illustrates an areal display of distribution of mass density information on a developed photographic film (i.e. electrograph)

An example of the results of this process is illustrated in FIG. 5, wherein section 24 of the developed film 8 represents the recorded distribution of mass density of the sample, and section 26 corresponds to the reference attenuation levels of a calibration wedge. The developed film is characterized by high contrast and sharp detail revealing even small scale variations in the structure of the paper sample. The optical densities in the film, which correspond to the areal attenuation of the electron beams by the sample, can be digitized by such devices as a microdensitometer, a drum scanner, or a TV camera to give digital values for further data processing by a computer, if desired.

Figure 1B:
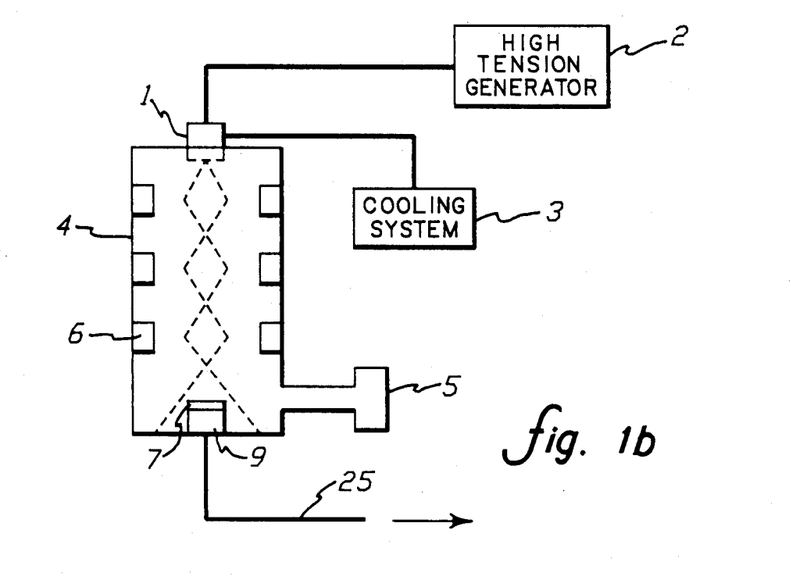
FIG. 1b is a schematic depiction of a system using a real-time electron beam detector assembly to measure the distribution of mass density of paper samples by electron beams.

FIG. 1b depicts schematically a system for measuring distribution of mass density using a real-time electron beam detector assembly. The same components used in FIG. 1a, except the photographic film, can be used in this version. The photographic film is replaced by a real-time electron beam detector assembly 9 such as a fluorescent screen attached to a vidicon, CCD, CID camera, a photo diode array, or similar detector which provides an electric output signal along line 25; otherwise the apparatus operates in a fashion identical to that of FIG. 1a.

Figure 2A:
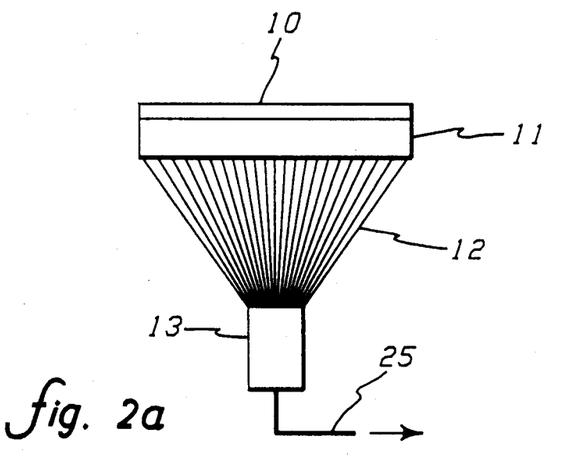
FIG. 2a illustrates a detector assembly using fiber optics.
Figure 2B:
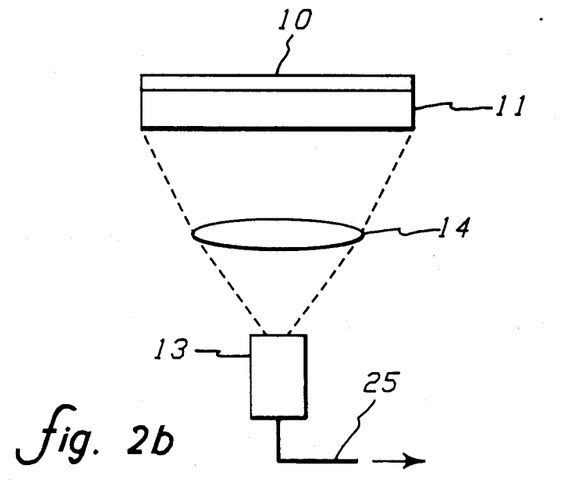
FIG. 2b illustrates a detector assembly using an optical lens system.

Exemplary detector configurations which are suitable for the system are shown in FIG. 2a and FIG. 2b. FIG. 2a depicts a detector assembly using fiber optics. The electron beams coming into the detector assembly excite the fluorescent screen 11 which is placed in the front of the detector unit and covered with conductive material 10 such as aluminum, copper, silver, palladium, or gold to avoid the charge up of the fluorescent screen. The fluorescent screen 11 converts the electron beams into visible, ultraviolet, or infrared light. The screen can be made of such materials as alkali halides (e.g. CsI), Yttrium aluminum garnet (YAG), and plastics which contain electron beam phosphors. The visible, ultraviolet, or infrared light converted from electron beams by the fluorescent screen is transferred to a TV camera 13 through fiber optics 12. The fiber optics can have a straight or a cone shape depending on the input and the output image sizes. The TV camera 13 detects the light and transforms it into an electric signal in known fashion. This electric signal is then transferred to an image data processing and displaying sub-system, described in more detail hereinafter, along an output line 25. This type of detector assembly reduces loss of light intensity and hence increases sensitivity.

FIG. 2b shows an alternative detector assembly using an optical lens system. The electron beams coming into the detector assembly excite the fluorescent screen 11 which is placed in the front of the detector and covered with conductive material 10 as described above. The fluorescent screen converts the electron beams into visible, ultraviolet, or infrared light and the same fluorescent screen as in FIG. 2a can be used here. The image which is formed on the output end of the fluorescent screen is transferred to the TV camera 13 with an optical lens 14. The TV camera transforms the light into electric signals and the electric signals are then transferred to an image data processing and displaying sub-system along output line 25. This type of detector assembly enables one to change the size of the area of interest by changing the distance between the fluorescent screen, the optical lens, and the TV camera.

Figure 3:
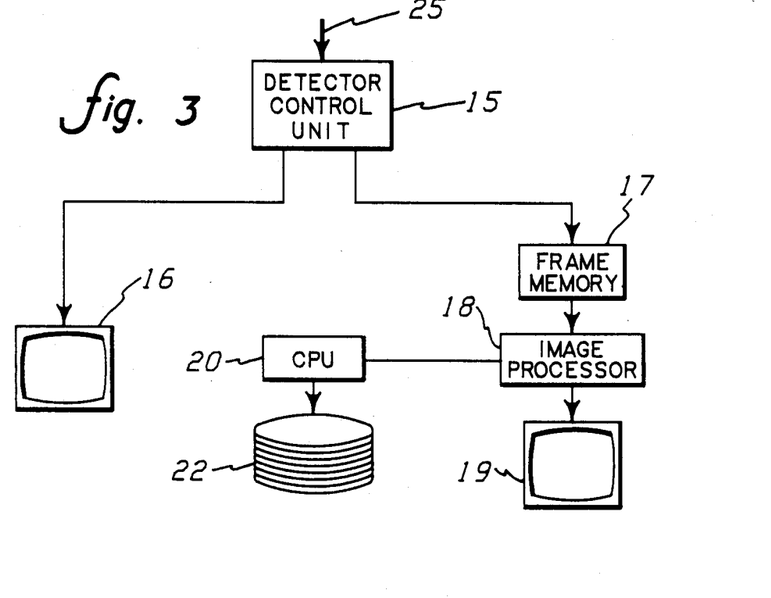
FIG. 3 is a schematic of a data processing and displaying sub-system useful in the mass density measuring method of the invention.

FIG. 3 shows an example of an image data processing and displaying sub-system. The electric signal generated by the camera 13 is transferred along line 25 to a detector control unit 15. The captured real-time image can be displayed by a TV monitor 16 which is connected to the detector control unit 15 or stored in digital form in a frame memory 17. The stored image can be processed by an image processor 18, e.g. to enhance contrast, extract a feature or perform a statistical analysis, and then displayed by a TV monitor 19. The image processor can be hosted by a computer system 20 which is equipped with a CRT terminal 21 to control the computer and the image processor, and a magnetic disk unit 22 to store the image permanently. The basis weight calibration is accomplished with the image processor 18 by transforming the digitized optical density data stored in the frame memory 17 into the basis weight with reference to the standard wedge mentioned above. This system enables a real-time measurement of mass density distribution of the sample.

Specific examples of apparatus and techniques which have been or can be employed to measure the distribution of mass density of a sample in accordance with the principles of the present invention, will now be discussed. Since the energy attenuation of electrons in a Mylar film is very similar to that in cellulose, experimental studies have employed Mylar film.

EXAMPLE 1

Electron beam generator: JEOL JEM-2000EX Transmission Electron Microscope Accelerating voltage: 80, 100, 150, 200 kV
Current density: 30 pA/cm$^2$
Exposure time: 1.0 second
Sample: Mylar film (0-180 g/m$^2$, 5 mm×5 mm)
Photographic film: Mitsubishi Electron Microscopy Film The image of attenuated electron beams from the sample was recorded on the photographic film with a system arranged as shown in FIG. 1a. The photographic film was developed in a standard fashion and the optical densities in the film were measured by a MacBeth RD-504 microdensitometer. The optical density data was normalized by adjusting the initial intensity (basis weight=0 g/m$^2$) to 1.0 and then plotted against the sample basis weight with the results shown in FIG. 4a.

Figure 4A:
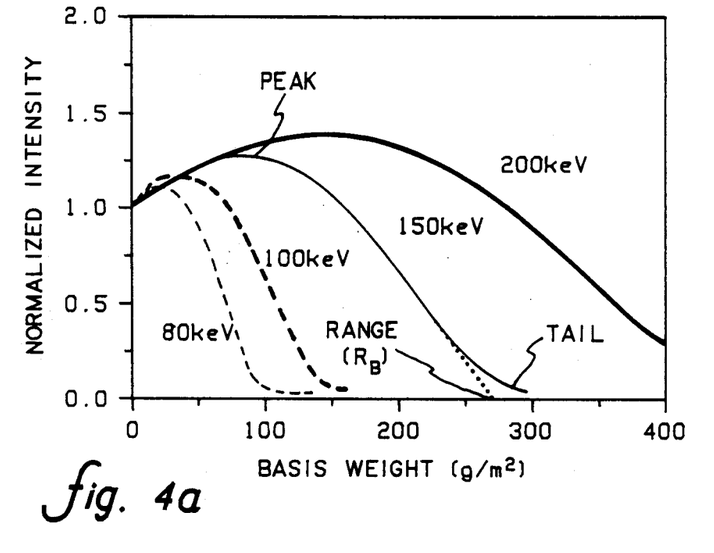
FIG. 4a is a graphical depiction of an example of a basis weight calibration curve using a photographic film.

FIG. 4a indicates that a wide range of basis weight (0-400 g/m$^2$) can be detected with this system and that the sensitivity of the measuring instrument can be optimized for a particular subrange of basis weight by selecting or changing the accelerating voltage. As shown in FIG. 4a, the energy attenuation curves exhibit peaks and tails which are believed to be attributable to the structure of the photographic film, and to the fluctuation of collision probability for each electron, respectively. The measurable basis weight at a particular accelerating voltage is limited between the peak and the range (RB). By using different energy levels, the anomolous high values (i.e. peaks) can be avoided. As the electron energy decreases, the basis weight resolution and electrograph contrast increases. Instead of using a single quick burst of equal energy electron beams, the sample can be exposed to beams at different energy levels either simultaneously or sequentially in order, for example, to extend the measurable basis weight range.

EXAMPLE 2

Figure 4B:
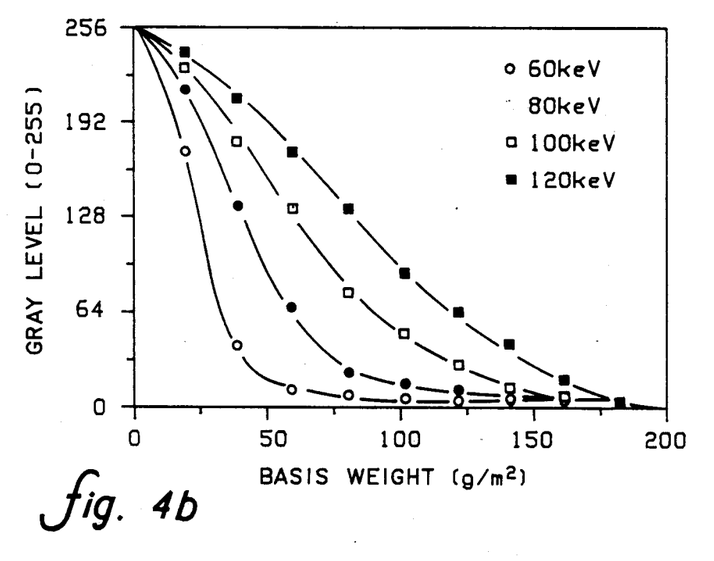
FIG. 4b is a graphical depiction of an example of a basis weight calibration curve using a real-time electron beam detector.

Electron beam generator: Philips EM 400 Transmission Electron Microscope Accelerating voltage: 60, 80, 100, 120 kV
Current density: 50 pA/cm$^2$
Exposure time: less than 1.0 second (real-time image acquisition)
Sample: Mylar film (0-180 g/m$^2$, 3 mm×3 mm)
Electron beam detector: Gatan Model 673 TV monitoring system The attenuated electron beams from the sample were detected by a Gatan Model 673 TV monitoring system with the setup shown in FIG. 1b, and the electric signal from the detector assembly was converted into 256 gray levels by a Coreco Oculus 200 image processing board hosted by an IBM-PC personal computer. The data was normalized to give 256 gray levels in full scale and plotted against the sample basis weight as shown in FIG. 4b. FIG. 4b indicates that a wide range of basis weight can be measured in real-time with this system and the basis weight resolution is better than that of the system using a photographic film. The difference in shape between the basis weight calibration curves of FIG. 4b and those of FIG. 4a is a result of a difference in detector response.

Figure 6:
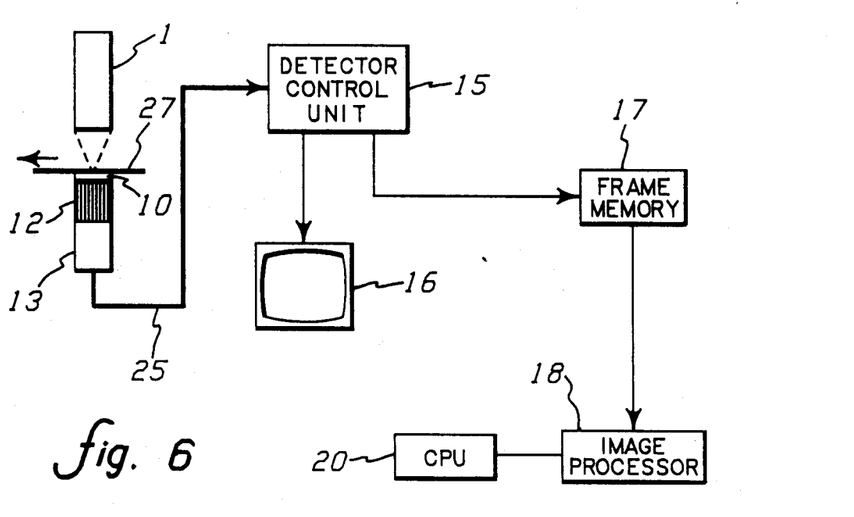
FIG. 6 is a schematic depiction of an on-line measuring system constructed in accordance with the principles of the present invention.

FIG. 6 illustrates schematically a potential on-line real-time electron beam imaging system. Moving paper web 27 passes through an imaging station between electron gun 1 and a real-time detector assembly similar to that shown in FIG. 2a. The detector assembly includes a fluorescent screen 10 linked by fiber optics 12 to a CCD camera or photodiode array 13. The electric output signal from the detector assembly is conveyed by line 25 to a control unit 15 which in turn is connected to a CRT 16 and frame memory 17. Image processor 18 controlled by computer 20 is employed to process the digital image stored in frame memory 17. By using an electron gun 1 which produces intense electron beams, the on-line measuring system can be operated in the air rather than in a vacuum.

From the foregoing, it will be apparent that a new method for measuring distribution of mass density of paper and other materials has been developed which represents a dramatic breakthrough in this art. Imaging by electron beams, in accordance with the present invention, is much quicker and gives better contrast than conventional beta-radiographs. In addition, paper, organics and inorganics of basis weight in the range of 0–400 g/m² or more can be imaged. Basis weight for conventional beta-radiography is typically limited to 100 g/m². Further, the health risk associated with the prior art is avoided. The present invention affords greater control and finer detail than other objective techniques. It facilitates real-time data processing and presents the possibility of on-line measurement, all at reasonable costs and with improved accuracy.

Although various embodiments have been described and depicted herein, those skilled in this art will recognize that various modifications, substitutions, additions and the like can be made without departing from the spirit of the invention, the scope of which is defined by the claims appended hereto.

What is claimed is:

1. A method for rapidly determining the distribution of mass density of a paper sample, comprising the steps of:
    exposing the sample to electron beams generated by an electron gun;
    detecting the attenuated intensity of the electron beams after the beams have traversed the sample with a detector located directly behind and adjacent to the sample, and providing an output representative of the attenuated intensity; and
    processing the detector output to obtain distribution of mass density information for the sample.

2. The method of claim 1 wherein said exposing step comprises simultaneously exposing a designated test area on the sample to a uniform intensity distribution of electron beams, and said detector is an areal detector located directly behind said test area.

3. The method of claim 1 further comprising the step of creating a vacuum environment along the path of the electron beams.

4. The method of claim 2 wherein said detecting step comprises using a photographic media as the detector, and said processing step comprises developing the photographic media.

5. The method of claim 2 wherein said detecting step comprises using a real time electron beam detector assembly as the detector.

6. The method of claim 5 wherein said detecting step comprises converting detected electron beam intensity into light intensity and then into a corresponding electric signal; and the processing step comprises processing said electric signal with computer controlled data processing and displaying apparatus.

7. The method of claim 1 wherein said exposing step comprises exposing the sample to electron beams of different energy levels.

8. The method of claim 1 wherein said sample is exposed to electron beams with energies in the range of 50 keV to 200 keV for an exposure time on the order of one second or less.

9. The method of claim 1 wherein a calibration wedge containing sites of known different basis weight having a similar mass absorption coefficient to that of paper, is simultaneously exposed to the electron beams with the sample to provide reference levels for basis weight calibration for the sample.

10. The method of claim 1 wherein the processing step includes production of an areal depiction of distribution of mass density from the detector output.

11. The method of claim 1 wherein the processing step comprises digitizing the detector output.

12. The method of any one of claims 1, 3, 4, 5, 7, 8 or 9, wherein the sample is in contact with the detector.

13. A method of determining the distribution of mass density of a sample, comprising the steps of:
    providing an electron beam gun;
    irradiating a test area of a sample under test with a burst of electron beams from said electron gun;
    providing an areal electron beam detector immediately behind and adjacent to the test area of the sample;
    detecting with said detector the intensity levels of electron beams emerging from said test area; and
    processing said intensity levels to provide distribution of mass density information for the test area of said sample.

14. The method of claim 13 further comprising the step of adjusting the energy level of the electron beams to correspond with a desired range of measurable basis weight.

15. The method of claim 13 wherein the sample is an organic material.

16. The method of claim 15 wherein the sample is a cellulose material.

17. The method of claim 16 further comprising the steps of:
    enclosing said gun and sample within a vacuum chamber, and evacuating air from said chamber while irradiating the sample.

18. The method of claim 16 wherein said irradiating step includes exposing the sample to electron beams of different energy levels.

19. The method of any one of claims 12, 13, 15 or 16, wherein the detector is in contact with the test area of the sample.

20. Apparatus for determining the distribution of mass density of a sample comprising:
    an electron beam gun;
    means for directing a burst of electron beams from said electron gun onto a test area of a sample under test;
    electron beam detector means located immediately behind and adjacent to the test area for detecting the intensity levels of electron beams emerging from said test area; and
    processing means for processing said intensity levels to derive distribution of mass density information for the test area of said sample.

21. The apparatus of claim 20 further comprising:
    a vacuum chamber enclosing the path of said electron beams between the electron gun and the sample, and means for evacuating air from said chamber while the sample is being irradiated; and
    means for controlling the energy level and divergence of said electron beams.

22. The apparatus of claim 18 wherein said processing means comprises means for converting said intensity levels into digital form and means for storing, processing and displaying the distribution of mass density information.

23. The apparatus of any one of claims 18, 19 or 20, wherein the detector means is in contact with said test area.

* * * * *

UNITED STATES PATENT AND TRADEMARK OFFICE
CERTIFICATE OF CORRECTION

PATENT NO. : 4,975,578

DATED : December 4, 1990

INVENTOR(S) : Tomimasu, et al.

It is certified that error appears in the above-identified patent and that said Letters Patent is hereby corrected as shown below:

Column 8

Claim 19, line 1 should read as follows:
--The method of any one of claims 13, 14, 16 or 17,--.

Claim 22, line 1, substitute --20-- for "18".

Claim 23, line 1 should read as follows:
--The apparatus of any one of claims 20, 21 or 22,--.

Signed and Sealed this

Eleventh Day of August, 1992

Attest:

DOUGLAS B. COMER

*Attesting Officer*　　　　*Acting Commissioner of Patents and Trademarks*